(12) United States Patent
Nakai et al.

(10) Patent No.: US 9,149,240 B2
(45) Date of Patent: Oct. 6, 2015

(54) X-RAY CT APPARATUS AND DATA TRANSMISSION METHOD OF X-RAY CT APPARATUS

(71) Applicants: Kabushiki Kaisha Toshiba, Minato-ku (JP); Toshiba Medical Systems Corporation, Otawara-shi (JP)

(72) Inventors: Hiroaki Nakai, Nasushiobara (JP); Tooru Kato, Nasushiobara (JP); Kanta Kobuchi, Otawara (JP)

(73) Assignees: Kabushiki Kaisha Toshiba, Minato-ku (JP); Toshiba Medical Systems Corporation, Otawara-shi (JP)

( * ) Notice: Subject to any disclaimer, the term of this patent is extended or adjusted under 35 U.S.C. 154(b) by 166 days.

(21) Appl. No.: 13/855,327

(22) Filed: Apr. 2, 2013

(65) Prior Publication Data

US 2013/0216018 A1 Aug. 22, 2013

Related U.S. Application Data

(63) Continuation of application No. PCT/JP2012/065906, filed on Jun. 21, 2012.

(30) Foreign Application Priority Data

Jul. 6, 2011 (JP) ................................ 2011-150497

(51) Int. Cl.
*A61B 6/03* (2006.01)
*A61B 6/00* (2006.01)
(Continued)

(52) U.S. Cl.
CPC ............... *A61B 6/032* (2013.01); *A61B 6/4078* (2013.01); *A61B 6/4233* (2013.01); *G06F 19/3406* (2013.01); *G06T 7/0012* (2013.01)

(58) Field of Classification Search
USPC ........................................................ 378/4–20
See application file for complete search history.

(56) References Cited

U.S. PATENT DOCUMENTS 7,844,097 B2 11/2010 Wegener
2003/0156679 A1* 8/2003 Mori et al. .................... 378/4
(Continued)

FOREIGN PATENT DOCUMENTS

CN 101883525 A 11/2010
JP 05-212027 8/1993
(Continued)

OTHER PUBLICATIONS

Combined Chinese Office Action and Search Report issued Jun. 25, 2014 in Patent Application No. 201280000702.9.
(Continued)

*Primary Examiner* — Hoon Song
(74) *Attorney, Agent, or Firm* — Oblon, McClelland, Maier & Neustadt, L.L.P.

(57) ABSTRACT

According to one embodiment, an X-ray CT apparatus includes a data acquiring unit, a data processing unit and a data transmitting unit. The data acquiring unit is configured to expose an X-ray to an object, acquire detection data of the X-ray having transmitted the object and compress the detection data to generate compressed data. The data processing unit is configured to generate X-ray CT image data of the object based on the compressed data transmitted from the data acquiring unit through a transmission line. The data transmitting unit is configured to transmit uncompressed detection data of an X-ray to the data processing unit through the transmission line according to information from an input device.

13 Claims, 5 Drawing Sheets

(51) Int. Cl.
*G06T 7/00* (2006.01)
*G06F 19/00* (2011.01)

(56) References Cited

U.S. PATENT DOCUMENTS

| 2010/0128998 A1* | 5/2010 | Wegener et al. ............... 382/248 |
| 2012/0213328 A1* | 8/2012 | Dolazza et al. ................. 378/19 |

FOREIGN PATENT DOCUMENTS

| JP | 10-127616 | 5/1998 |
| JP | 2004-193818 | 7/2004 |
| JP | 2006-006805 | 1/2006 |
| JP | 2007-097977 | 4/2007 |
| JP | 2011-505228 | 2/2011 |
| JP | 2011-188157 | 9/2011 |

OTHER PUBLICATIONS

International Search Report mailed Aug. 21, 2012 for PCT/JP2012/065906 filed Jun. 21, 2012.
International Written Opinion mailed Aug. 21, 2012 for PCT/JP2012/065906 filed Jun. 21, 2012.
English translation of the International Preliminary Report on Patentability and Written Opinion issued Jan. 16, 2014, in PCT/JP2012/065906 filed Jun. 21, 2012.

\* cited by examiner

ABSTRACT# X-RAY CT APPARATUS AND DATA TRANSMISSION METHOD OF X-RAY CT APPARATUS

CROSS REFERENCES TO RELATED APPLICATIONS

This is a continuation of Application PCT/JP2012/65906, filed Jun. 21, 2012.

This application is based upon and claims the benefit of priority from Japanese Patent Application No. 2011-150497, filed Jul. 6, 2011; the entire contents of which are incorporated herein by reference.

FIELD

Embodiments described herein relate generally to an X-ray CT (computed tomography) apparatus and a data transmission method of an X-ray CT apparatus.

BACKGROUND

In the X-ray CT apparatus, a helical scan method and a multi-detector method are adopted widely in order to obtain tomographic images of an object three-dimensionally and precisely. For this reason, a rotation speed of a scanner becomes high, the number of rows of a detector increases and a size of data output from a detector becomes huge. Therefore, it is important to suppress increase in the cost for data communications and data storages in an X-ray CT apparatus.

Accordingly, a method of compressing original data, output from the rotational part of the gantry in the detector side, in the DAS (Data acquisition system) is suggested for reduction of the data size to be transmitted in the X-ray CT apparatus. It is mainly between the rotational part and an irrotational part in the gantry and between the irrotational part of the gantry and the data processing system, for various correction processing and image reconstruction processing, that data transmission is performed in the X-ray CT apparatus.

In these parts with data transmission, it is necessary to guarantee the transmission rates in order to avoid a serious failure of data loss. The cost for a data transmission depends on the transmission rate to be guaranteed. Therefore, in order to suppress the increase in transmission cost by information compression, it is necessary to compress data by an information compression method which can secure a predetermined compression ratio not so as to exceed the transmission rate guaranteed for the data transmission system.

By a reversible information compression method, a compression ratio cannot be guaranteed theoretically although the information included in data is reservable. For example, truly random data cannot be compressed at all by a reversible information compression method. Therefore, a reversible information compression method cannot guarantee a transmission rate smaller than that in the case of transmitting the data before the information compression. In other words, the data transmission portion must guarantee the transmission rate in the case of transmitting the data before the compression. For this reason, the transmission cost cannot be reduced if a reversible information compression method is used.

On the other hand, if data is compressed by the irreversible information compression method, the transmission rate can be guaranteed by adjustment of the compression ratio. Therefore, it is necessary to use an irreversible compression method as the information compression method in order to guarantee a transmission rate.

PRIOR TECHNICAL LITERATURE

[Patent literature 1] JPA2007-97977
[Patent literature 2] JPA H05-212027
[Patent literature 3] JPA H10-127616

When data is compressed by an irreversible information compression method, there is a problem that the error due to the compression arises in the data after the information compression though the transmission rate of the data can be guaranteed. For this reason, when a failure, such as a noise or an error, arises in data in the detector or the DAS, it becomes difficult to distinguish whether the failure is caused by the information compression or the device such as the detector or the DAS.

That is, the conventional X-ray CT apparatus throws up the problem that it becomes difficult to perform behavior verifications of the detector and the DAS when data is compressed by an irreversible information compression method.

Moreover, whether the information compression is reversible or irreversible, it is desired to acquire data necessary for generation of X-ray CT image data or the like promptly when a failure caused by the information compression has arisen in data.

Accordingly, it is an object of the present invention to provide an X-ray CT apparatus and a data transmission method of an X-ray CT apparatus which can restart an imaging promptly when a failure, such as a noise or an error, possibly caused by an information compression has arisen in data.

DETAILED DESCRIPTION

In general, according to one embodiment, an X-ray CT apparatus includes a data acquiring unit, a data processing unit and a data transmitting unit. The data acquiring unit is configured to expose an X-ray to an object, acquire detection data of the X-ray having transmitted the object and compress the detection data to generate compressed data. The data processing unit is configured to generate X-ray CT image data of the object based on the compressed data transmitted from the data acquiring unit through a transmission line. The data transmitting unit is configured to transmit uncompressed detection data of an X-ray to the data processing unit through the transmission line according to information from an input device.

Further, according to another embodiment, an X-ray CT apparatus includes a data acquiring unit, a data processing unit and a data transmitting unit. The data acquiring unit is configured to expose an X-ray to an object, acquire detection data of the X-ray having transmitted the object and compress the detection data by an irreversible compression method to generate compressed data. The data processing unit is configured to generate X-ray CT image data of the object based on the compressed data transmitted from the data acquiring unit through a transmission line. The data transmitting unit is configured to compress reference data by the irreversible compression method according to information from the input device to transmit the compressed reference data to at least one of the data processing unit and the input device through the transmission line with a transmission rate not more than a transmission rate of the compressed data. A compression result of the reference data by the irreversible compression method is known.

Further, according to another embodiment, a data transmitting method of an X-ray CT apparatus includes compressing detection data of an X-ray having transmitted an object by an irreversible compression method to generate compressed data; transmitting the compressed data through a transmission line; and transmitting uncompressed detection data of an X-ray as verification data through the transmission line with a transmission rate not more than a transmission rate of the compressed data according to information from the input device.

An X-ray CT apparatus and a data transmission method of an X-ray CT apparatus according to embodiments of the present invention will be described with reference to the accompanying drawings.

Figure 1:
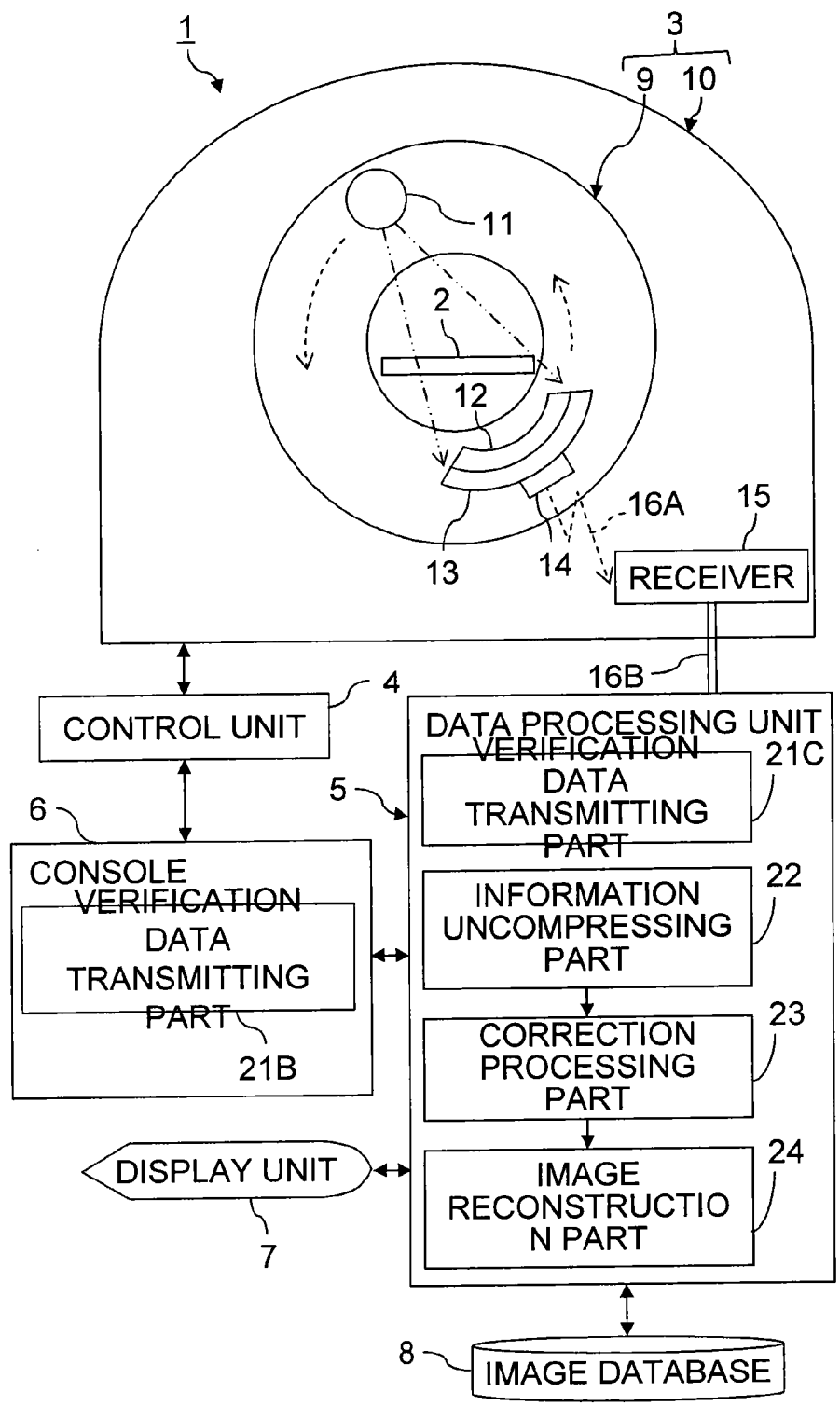
FIG. 1 is a block diagram of an X-ray CT apparatus according to an embodiment of the present invention.

FIG. 1 is a block diagram of an X-ray CT apparatus according to an embodiment of the present invention.

The X-ray CT apparatus 1 includes a bed 2, a gantry 3, a control unit 4, a data processing unit 5, a console 6, a display unit 7, and an image database 8. The bed 2 is arranged inside the cylindrical gantry 3, and can be sent in the gantry 3 in a state where an object has been set. The gantry 3 has a rotational part 9 and an irrotational part 10, and an X-ray exposure part 11, an X-ray detector 12, a DAS 13, and a transmitter 14 are built in the rotational part 9. On the other hand, a receiver 15 is set in the irrotational part 10 of the gantry 3. Then, the transmitter 14 is connected with the receiver 15 by a data transmission line 16A while the receiver 15 is connected with the data processing unit 5 by a data transmission line 16B.

The X-ray exposure part 11 is an apparatus which includes an X-ray tube and exposes an X-ray toward the object set on the bed 2 under a voltage application from a high voltage generator to the X-ray tube.

The X-ray detector 12 is arranged opposite to the X-ray exposure part 11 so that the bed 2 lies between the X-ray detector 12 and the X-ray exposure part 11. The X-ray detector 12 is an apparatus which detects the X-ray exposed from the X-ray tube of the X-ray exposure part 11 and having transmitted the object. The X-ray detector 12 in recent years includes many rows and X-ray detection elements arranged two-dimensionally.

Then, the system consisting of these elements is configured to rotate the X-ray exposure part 11 and the X-ray detector 12 around an object together with the rotational part 9 to expose an X-ray beam, having a three dimensional sectorial shape, to the object from directions within 360 degrees by the X-ray exposure part 11 and detect the X-ray, having transmitted the object, by the X-ray detector 12.

Figure 2:
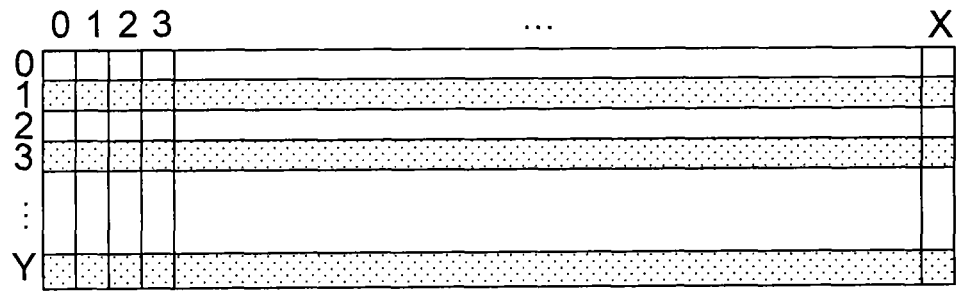
FIG. 2 is a view showing arrangement of the X-ray detection elements included in the X-ray detector shown in FIG. 1.

FIG. 2 is a view showing arrangement of the X-ray detection elements included in the X-ray detector 12 shown in FIG. 1.

As shown in FIG. 2, plural X-ray detection elements for two-dimensionally detecting an X-ray having transmitted an object are arranged on the X-ray detector 12. In FIG. 2, the horizontal direction is the fan angle direction parallel to the rotational plane of the rotational part 9 of the gantry 3 and is also referred to as the channel direction. Meanwhile, the vertical direction is the cone angle direction perpendicular to the rotational plane of the rotational part 9 of the gantry 3 and is also referred to as the row direction. Therefore, the body axis direction of an object is the row direction of the X-ray detection elements.

FIG. 2 shows an example of the X-ray detector 12 which has an X number of the X-ray detection elements in the fan angle direction and a Y number of the X-ray detection elements in the cone angle direction. When an X-ray is detected once at a certain rotation angle by the X-ray detector 12 which has the above-mentioned composition, an X-ray detection data group which has an array corresponding to the arrangement of the X-ray detection elements is acquired.

The X-ray detection data group corresponding to the arrangement of the X-ray detection elements is called view data. Since the view data correspond to the arrangement of the X-ray detection elements, the view data consist of data having X channels and Y rows. Since the X-ray detector 12 rotates with the rotational part 9, the view data are acquired to the number of the angles of the rotational part 9 at which data acquisitions are performed. The angles of the rotational part 9 equivalent to the number of the pieces of the view data are counted using the unit [view].

Figure 3:
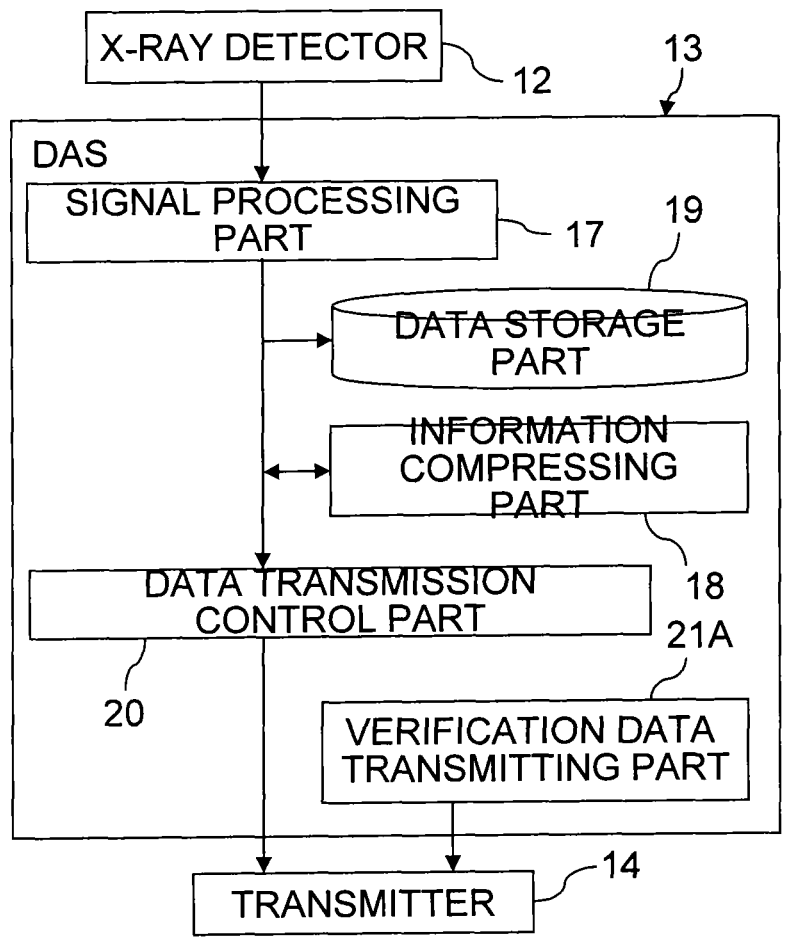
FIG. 3 is a functional block diagram of the DAS shown in FIG. 1.

FIG. 3 is a functional block diagram of the DAS 13 shown in FIG. 1.

The DAS 13 includes a signal processing part 17, an information compressing part 18, a data storage part 19, a data transmission control part 20, and a verification data transmitting part 21A.

The signal processing part 17 has a function to acquire X-ray detection data output as electric signals from the respective X-ray detection elements of the X-ray detector 12 to generate digitized projection data corresponding to the respective X-ray detection elements by signal processing, such as an amplification, integral processing, an A/D (analog to digital) conversion processing, and a logarithmic transformation processing. The signal processing part 17 also has a function to output the generated projection data to the data processing unit 5 through the transmission pathway including the transmitter 14, the receiver 15, and the data transmission lines 16A, 16B. That is, the functions of the signal processing part 17 are fundamental functions which the normal DAS 13 has.

In addition, the DAS 13 is configured to switch operations under the compressed mode and the uncompressed mode according to direction information input from the console 6. In any of the compressed mode and the uncompressed mode, it is desirable to transmit data from the DAS 13 with a transmission rate not more than a transmission rate guaranteed in the transmission pathway including the transmitter 14, the receiver 15, and the data transmission lines 16A, 16B.

The compressed mode is the operational mode of the DAS 13 which performs information compression processing for compressing a size of data to be transmitted to the data processing unit 5 into 1/n and outputs the compressed data to the data processing unit 5. Note that, n is an arbitrary real number larger than 1. Therefore, the compressed mode is selected for a normal imaging of an object.

In order to guarantee the data compression rate of 1/n so that a transmission rate not more than the transmission rate guaranteed in the transmission pathway is secured, it is necessary to perform irreversible information compression processing. It is because any reversible information compression processing cannot guarantee a compression ratio theoretically. For example, by reversible compression processing, random data cannot be compressed. Accordingly, the information compressing part 18 has a function to perform a data compression not only by a reversible compression method but an arbitrary irreversible compression method.

The data compression processing by an irreversible compression method consists of processing steps which mainly include signal transformation processing, quantization processing, and coding processing. For example, the JPEG (Joint Photographic Experts Group) format, the JPEG 2000 format, and the JPEG-LS format are known as irreversible compression methods of image data. The JPEG format is an irreversible compression method to perform a discrete cosine transform and use Huffman coding. Meanwhile, the JPEG 2000 format is an irreversible compression method to perform a discrete wavelet transform and use the arithmetic coding. Moreover, the JPEG-LS format is an irreversible compression method to perform correlation prediction between pixels and use Golomb-Rice coding.

In the information compression processing by an irreversible compression method represented by these, data can be compressed irreversibly with a predetermined compression ratio by controlling the amounts of information omitted in the signal transformation processing and the quantization processing. That is, the data compression rate of 1/n can be guaranteed so that a transmission rate not more than the transmission rate guaranteed in the transmission pathway is secured.

Figure 4:
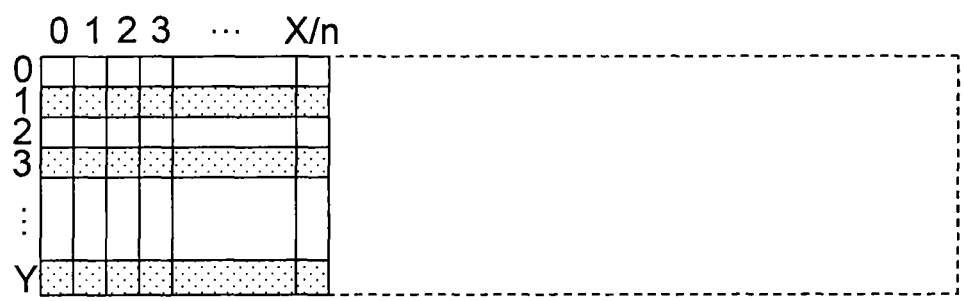
FIG. 4 is a schematic view of compressed data obtained by compressing X-ray detection data, acquired by the X-ray detector shown in FIG. 2, into 1/n.

FIG. 4 is a schematic view of compressed data obtained by compressing X-ray detection data, acquired by the X-ray detector 12 shown in FIG. 2, into 1/n.

In FIG. 4, the horizontal direction is the channel direction of the X-ray detection elements and the vertical direction is the row direction of the X-ray detection elements. When the information compression processing by an irreversible compression method is performed to compress data in the respective rows of the X-ray detection elements having the X channels and Y rows as shown in FIG. 4, the compression ratio of 1/n can be guaranteed. Therefore, in the transmission pathway from the DAS 13 to the data processing unit 5, what is necessary will be just to guarantee at least the transmission rate of compressed data which have been compressed into 1/n. In other words, the transmission pathway can be formed using the data transmission lines 16A and 16B which guarantee the transmission rate of the compressed data which have been compressed into 1/n.

Note that, the compressed data are to contain X/n pieces of data per row and to have the information for the X channels by the X/n pieces of data on an average. Therefore, the horizontal position of the compressed data does not agree with the position in the channel direction of the X-ray detection elements. Moreover, in the information compression processing by an irreversible compression method, all the amount of information before the compression cannot be saved. For this reason, the compressed data and the uncompressed data obtained by uncompressing the compressed data into data for the X channels by uncompressing processing involve errors due to the irreversible compression processing.

On the other hand, the uncompressed mode is the operational mode of the DAS 13 which outputs uncompressed data to the data processing unit 5 as data for behavior verification of the DAS 13 or data for generation of X-ray CT image data of an object without an information compression. Namely, the uncompressed mode is the mode for a case where a defect, such as a noise or an error, has arisen in data, to verify whether the defect is due to the information compression processing in the information compressing part 18 or the other cause such as another portion of the DAS 13 or the X-ray detector 12, and to restart an imaging promptly to generate X-ray CT image data.

Therefore, the uncompressed mode is selected mainly when a failure, such as a noise or an error, has arisen to data output from the DAS 13. The uncompressed data generated in the uncompressed mode are transmitted to the data processing unit 5 preferably with a transmission rate not more than the low transmission rate for the compressed data guaranteed in each of the data transmission lines 16A and 16B.

The data storage part 19 and the data transmission control part 20 are included in the DAS 13 for operation of the uncompressed mode described above.

The data storage part 19 has a function to store the data, before the information compression, acquired in the DAS 13 as data for behavior verification of the DAS 13 or data for generation of X-ray CT image data of an object. For that purpose, the data storage part 19 has a function to store uncompressed data having a quantity necessary for behavior verification of the DAS 13 or image reconstruction processing of X-ray CT image data as verification data or spare data. As the verification data for the DAS 13, a part or all of detection data of an X-ray that have transmitted a desired object, such as air or a phantom, can be used.

When only the verification data for the DAS 13 are stored, the data storage part 19 can be made by a storage which can store data, acquired by the X-ray detector 12 with rotating the rotational part 9 of the gantry 3 one time, for behavior verification, for example. When the rotational part 9 of the gantry 3 is rotated one time, about hundreds to thousands [view] of pieces of the view data are acquired. In this case, the capacity of storage required for storing view data for one rotation is hundreds [MB] to a few [GB].

Thus, a data size of data for behavior verification of the DAS 13 is very small compared with living body data acquired by rotating the X-ray detector 12 plural times for examination of an object. Therefore, an existing storage, such as a RAM (Random Access Memory), usually equipped with the DAS 13 can be simply used as the data storage part 19. Alternatively, if a mass storage is used for the data storage part 19, uncompressed data required for generation of X-ray CT image data can be stored.

The data transmission control part 20 has a function to control uncompressed data output from the DAS 13 so that the transmission rate of the uncompressed data for verification transmitted from the DAS 13 to the data processing unit 5 becomes not more than each of the transmission rates guaranteed in the data transmission lines 16A and 16B in the uncompressed mode. More specifically, the data transmission control part 20 has a function to transmit uncompressed data with a time division or a spatial division from the DAS 13 to the subsequent data transmission lines 16A and 16B in the uncompressed mode.

In case of using the uncompressed data stored in the data storage part 19 as data for behavior verification of the DAS 13 or data for generation of X-ray CT image data, the data transmission control part 20 is configured to output the uncompressed data acquired from the data storage part 19 with a time division so that the transmission rate becomes not more than each of the transmission rates guaranteed in the data transmission lines 16A and 16B.

For example, if a time division of the uncompressed data for one rotation into n pieces of divided data for every view data is performed, the transmission rate of the uncompressed data can be compressed into 1/n. In this case, all the uncompressed data can be transmitted to the data processing unit 5 in a transmission time for the case of transmitting the data obtained by rotating the rotational part 9 n times without a time division. Therefore, the uncompressed data subjected to the time division are transmitted from the DAS 13 to the data processing unit 5 in non-real-time.

When V pieces of the view data as data for one rotation of the X-ray detector 12 have been stored for behavior verification in the data storage part 19, the V pieces of the view data are divided into V×n pieces of the divided data in the data transmission control part 20.

Figure 5:
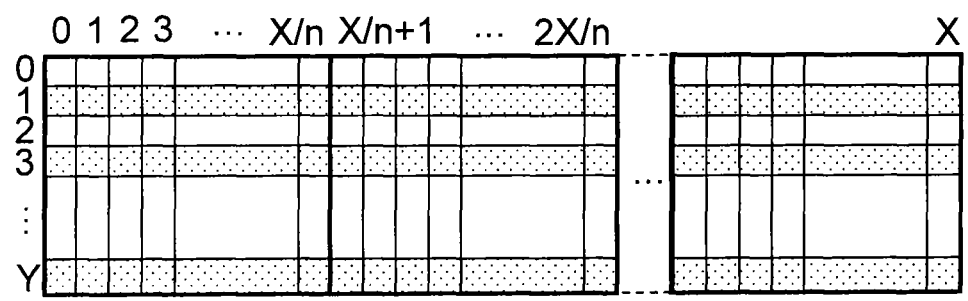
FIG. 5 is a schematic view of divided data obtained by dividing X-ray detection data, acquired by the X-ray detector shown in FIG. 2, into n pieces.

FIG. 5 is a schematic view of divided data obtained by dividing X-ray detection data, acquired by the X-ray detector 12 shown in FIG. 2, into n pieces.

In FIG. 5, the horizontal direction is the channel direction of the X-ray detection elements and the vertical direction is the row direction of the X-ray detection elements. As shown in FIG. 5, the two dimensional region corresponding to the X-ray detection elements having the X channels and of the Y rows can be divided in the channel direction into n equal areas.

That is, a divided area of which the width in the channel direction is from the zeroth channel to the X/n-th channel and the width in the row direction is from the zeroth row to the Y-th row can be made. When a divided area having the same size is created sequentially in the channel direction, the divided areas consisting of the divided area, of which position in the channel direction is from the X/n+1-th channel to the 2X/n-th channel, up to the divided area, of which position in the channel direction is from the (n−1)X/n+1-th channel to the X/n-th channel can be obtained. As a result, the n divided areas each having an equal width can be made.

As a simple example, when n=2, i.e., the two dimensional region corresponding to the X-ray detection elements is divided into two areas, the two dimensional region can be divided into the first divided area consisting of the first half channels and the second divided area consisting of the second half channels.

Moreover, n divided areas can be also similarly created in the row direction. For example, when the two dimensional region corresponding to the X-ray detection elements is divided into two areas, the two dimensional region can be divided into the first divided area consisting of the first half rows and the second divided area consisting of the second half rows.

When the two dimensional region corresponding to the X-ray detection elements is divided into two or more areas, the data corresponding to each area can be used as the uncompressed divided data. Since the number of the pieces of the view data is V, the number of the pieces of the divided data and the divided areas is V×n.

The data size per one piece of the divided data obtained as described above becomes 1/n of the size of the view data before the division. Therefore, it becomes possible to transmit the view data consisting of all the pieces of the divided data from the DAS 13 to the data processing unit 5 without compression by taking n times as long transmission period as that in the case where the view data are compressed into 1/n to be transmitted.

Note that, the acquired view data may be sequentially divided and transmitted from the DAS 13 to the data processing unit 5 without waiting for acquisition of all the V pieces of the view data and completion of storing all the V pieces of the view data in the data storage part 19.

The time division of the uncompressed view data can be performed by dividing the two dimensional region, corresponding to the X-ray detection elements, into plural areas according to an arbitrary rule besides the method mentioned above. Other examples of the time division method include a method on the basis of the row of the X-ray detection elements.

For example, when the data size of the uncompressed view data is compressed into ½, the uncompressed view data can be divided into the data from the X-ray detection elements in the odd number rows and those in the even number rows to be transmitted from the DAS 13 to the subsequent transmission pathway sequentially for every row. A generalized expression of the division method on the basis of the row of the X-ray detection elements is to transmit the data from the X-ray detection elements in the [Y/n]*n+(i mod n)-th row at the i-th. Note that, Y is the number of rows of the X-ray detection elements and [ ] is an operator which outputs the minimum natural number.

In addition, the data for behavior verification may be also created when a failure occurs to data. In this case, the data for behavior verification can be created using data from X-ray detection elements near the X-ray detection element corresponding to the data in which the failure has occurred, or data corresponding to a part of positions so that the rate of the view data at the rotation angle corresponding to the data in which the failure has occurred becomes high. That is, data corresponding to a part of positions selected unequally can be subjected to the time division to be transmitted from the DAS 13 as the uncompressed data for behavior verification. In this case, the part of positions can be selected so that the rate of the data corresponding to rotation angles, channels, and rows within a predetermined range becomes high.

Thus, the transmission rate of the uncompressed data can be guaranteed using the data transmission lines 16A and 16B to which the transmission rate corresponding to the compressed data compressed with the compression ratio of 1/n has been guaranteed.

On the other hand, in the uncompressed mode, data acquired in real time by the X-ray detector 12 with rotating the rotational part 9 may be also used as uncompressed data for behavior verification of the DAS 13 or generation of X-ray CT image data. In this case, it is desirable to perform a spatial division of the uncompressed data generated in the DAS 13 by the data transmission control part 20 so that the transmission rate of the uncompressed data becomes not more than that guaranteed in each of the data transmission lines 16A and 16B.

For example, the spatial division of the uncompressed data for behavior verification can be performed by acquiring and transmitting the view data for the behavior verification for one rotation, obtained by rotating the rotational part 9 one time in general, through n rotations of the rotational part 9. Similarly, the spatial division of the uncompressed data for generation of X-ray CT image data can be performed by acquiring and transmitting the view data for the generation of the X-ray CT image data for m rotations, obtained by rotating the rotational part 9 m times in general, through m×n rotations of the rotational part 9. Therefore, the spatial division of the uncompressed data in the data transmission control part 20 is performed in conjunction with a control of the rotational part 9.

The methods of dividing and acquiring data include a method of mechanically selecting data input into the DAS 13 by switching the switches connected respectively to the output sides of the X-ray detection elements included in the X-ray detector 12, and a method of selecting data output from the DAS 13 by filter processing which selects a part of X-ray detection data input into the DAS 13 from the X-ray detector 12 according to positions.

When the spatial division of the view data is performed by switching the switches between ON/OFF, the spatial division of the view data can be performed by outputting switching control signals for the switches from the data transmission control part 20 to the X-ray detector 12. On the other hand, when data output from the DAS 13 are set to data corresponding to a specific divided region, the spatial division of the view data can be performed by preparing a filter processing function, according to divided regions, in the data transmission control part 20.

Moreover, a method of dividing the view data is arbitrary. Therefore, the two dimensional region corresponding to the X-ray detection elements can be divided into two or more areas by a similar way to that in the case of the time division. Then, the data from one area can be acquired by one rotation for behavior verification or generation of X-ray CT image data. That is, the spatial division of the uncompressed data into pieces of data each having the size of 1/n can be performed by the method of acquiring data for every row of the X-ray detection elements or a method of acquiring data for every area on the X-ray detector 12 set on the basis of the row or channel of the X-ray detection elements.

Then, the uncompressed data for behavior verification or for generation of X-ray CT image data can be transmitted to the data processing unit 5 from the DAS 13 in real time with the transmission rate of 1/n by acquiring and transmitting data from a different divided area for every rotation of the rotational part 9.

As a concrete example, when n divided areas in the channel direction are created to each view data as shown in FIG. 5, the data from the zeroth channel to the X/n-th channel are acquired at all the rotational positions in the first rotation and transmitted to the data processing unit 5 without compression. In the next rotation, the data from the X/n+1-th channel to the 2X/n-th channel are acquired at all the rotational positions and transmitted to the data processing unit 5 without compression. Similarly, until the data from the (n−1)X/n+1-th channel to the X/n-th channel have been acquired and transmitted, the rotation of the rotational part 9 is repeated.

As a result, the data in all the channels can be transmitted to the data processing unit 5 by the n rotations of the rotational part 9 with 1/n of the transmission rate in case of acquiring the data by one rotation and transmitting the data without compression. Consequently, the uncompressed view data corresponding to all the channels for one rotation of the rotational part 9 can be transmitted through the data transmission lines 16A and 16B to which only the transmission rate of 1/n of the size of the uncompressed data corresponding to all the channels is guaranteed.

As another concrete example, in case of the spatial division of each view data into the two pieces of the data of the data corresponding to the odd number rows and the data corresponding to the even number rows, the view data divided into ½ can be transmitted to the data processing unit 5 with the transmission rate of ½ and without compression by acquiring and transmitting the data from the odd number rows in the first rotation, and by acquiring and transmitting the data from the even number rows in the second rotation.

When the spatial division on the basis of the row is generalized, what is necessary is just to acquire and transmit the data from the [Y/n]*n+(i mod n)-th row in the i-th rotation. Note that, Y is the total of the rows and [ ] is the operator which outputs the minimum natural number.

In addition, when a failure has occurred to data, the data for behavior verification may be also created using data corresponding to a part of positions like a case of the time division so that the rate of data from X-ray detection elements near the X-ray detection element corresponding to the data to which the failure has occurred or the view data at the rotation angle corresponding to the data to which the failure has occurred becomes high. That is, data corresponding to a part of positions can be subjected to the spatial division and transmitted as the uncompressed data for behavior verification from the DAS 13. In this case, the part of the positions can be selected unequally so that a rate of data corresponding to rotation angles, channels, and rows within a predetermined range becomes high.

As mentioned above, uncompressed data can be transmitted with a transmission rate lower than an original transmission rate in the uncompressed mode by either of the transmission control method which transmits the uncompressed data with the time division and with a delay or the transmission control method which transmits the uncompressed data, in real time, with the spatial division in conjunction with operation of the rotational part 9. However, the function to control transmission data by one transmission control method may be omitted.

Especially, if the function to transmit the uncompressed data with the time division and a delay is omitted, the data storage part 19 becomes omissible. Therefore, the operation under the uncompressed mode can be performed even if a mass storage which can store view data corresponding to one rotation or plural rotations of the rotational part 9 is not set in the DAS 13. For example, when 2000 [view] of the view data are acquired by one rotation, a storage which has about 1 [GB] of capacity is needed for transmitting the uncompressed data with the time division and a delay. However, by the omission of the data storage part 19, even the existing DAS 13 which does not include a sufficient storage can operate under the uncompressed mode.

Moreover, the mechanism for transmitting data to the subsequent part with time shifting may be unable to be provided due to the restrictions resulting from other controls and processing such as the control of data retransmission and a function to handle a power failure. In such a case, even if a mass storage is provided with the DAS 13, the delay transmission of data becomes difficult. However, the spatial division allows the operation under the uncompressed mode.

The verification data transmitting part 21A has a function to transmit the data for behavior verification irreversibly compressed as a reference pattern to the data processing unit 5 according to direction information input from the console 6 when an abnormality, such as a noise or an error, has occurred to data transmitted from the DAS 13 to the data processing unit 5. In addition, when a reference pattern has been transmitted from the console 6 or the data processing unit 5 to the DAS 13, the verification data transmitting part 21A is configured to verify the operation of the information compressing part 18 by comparing the reference pattern transmitted from the DAS 13 with the reference pattern received in the DAS 13.

The reference pattern for verification is data for distinguishing whether an abnormality occurred to data is due to the information compression processing in the information compressing part 18 or another element such as the X-ray detector 12 or another part in the DAS 13.

For that purpose, the reference pattern is prepared as data in which no lack of information arises by irreversible compression processing with the compression ratio of 1/n. The prepared reference pattern is stored in the verification data transmitting part 21A. In other words, data of which compression result by irreversible compression processing is known and always not more than 1/n can be used as the reference pattern.

For example, when the size of data output from the DAS 13 is 16 bits, data having random number values in the 8 bits from the zeroth bit up to the seventh bit and fixed values such as 0 in the 8 bits from the eighth bit up to the 15th bit can be made as a reference pattern. Then, the reference pattern having the 16 bits is to have only information for 8 bits having random number values, i.e., ½ information, from the viewpoint of an information amount.

Therefore, when the reference pattern of which 8 bits have the random number values is compressed by irreversible information compression processing in the information compressing part 18, the 8 bits having the fixed values can be compressed almost infinitely, i.e., the size can be compressed into zero, although the other 8 bits having the random number values are uncompressible at all. For this reason, the reference pattern can be compressed reversibly with the compression ratio of ½ without missing information even by an irreversible information compression.

Of course, a reference pattern having random number values in the 8 bits from the eighth bit up to the 15th bit or a reference pattern having random number values in arbitrary bits of data may be also created. Moreover, a compression ratio of a reference pattern may be set not only into ½ but an arbitrary compression ratio 1/n That is, a reference pattern which can be compressed irreversibly with a desired compression ratio 1/n within a reversible range can be created by using random numbers and fixed values.

Furthermore, a reference pattern can be also created using not only random number values but actually acquired data. For example, by masking a part of acquired data with a fixed value to generate bit mask data, a reference pattern which can be compressed irreversibly with a compression ratio not more than 1/n can be created. As a concrete example, data derived by zero padding of half of acquired data can be used as a reference pattern of which compression ratio is not more than ½.

In addition, when acquired data are 16 bits, pieces of data from two X-ray detection elements can be put in 16 bits of data by taking out only the latter 8 bits of the acquired data and bit packing (connecting as a bit row) of the latter 8 bits with data at an adjacent position. In this case, the latter 8 bits can be transmitted with a transmission rate of ½ without compression. Therefore, the latter 8 bits can be verified by the same way as that in the case where a spatial division is performed.

The bit positions to be taken out are not limited to the latter positions. Therefore, the former 8 bits or arbitrary bits out of the 16 bits may be taken out to be used for verification.

Thus, when acquired data are generally W bits, arbitrary W/n bits to be verified can be taken out. Then, corresponding bits can be verified by packing of pieces of data from n X-ray detection elements into a piece of data having W bits to transmit the packed piece of data with a 1/n rate without compression.

In addition, arbitrary data including a geometrical pattern, such as a checkered pattern and a striped pattern, or data corresponding to a natural image or a compound image can be used as a reference pattern.

Such a reference pattern can be previously stored as a test pattern also in one or both of the console 6 and the data processing unit 5 in addition to the verification data transmitting part 21A in the DAS 13. FIG. 1 shows the example of setting the verification data transmitting parts 21B and 21C, each having a similar function, in the console 6 and the data processing unit 5 respectively. Therefore, an irreversibly compressed reference pattern can be transmitted mutually between the verification data transmitting part 21A in the DAS 13 and each of the verification data transmitting parts 21B and 21C in the console 6 and the data processing unit 5.

Accordingly, in any of the console 6, the data processing unit 5, and the DAS 13, it becomes possible to compare a transmitted reference pattern with a received reference pattern. The comparison of the reference patterns can be performed in the compressed state and the uncompressed state. When the uncompressed reference pattern is compared with the other uncompressed one, the function to perform uncompressing processing of a reference pattern is prepared in each of the verification data transmitting parts 21A, 21B, and 21C.

Thus, an operation check and a failure analysis of the information compressing part 18 can be performed by the comparison of reference patterns transmitted mutually. Specifically, whether the information compressing part 18 has a failure or not can be verified by determining whether a transmitted reference pattern agrees with a received reference pattern or not, or whether a compression ratio of a transmitted reference pattern agrees with that of a received reference pattern or not. In this case, what is necessary is just to prepare the function to measure a compression ratio of a compressed reference pattern in each of the verification data transmitting parts 21A, 21B, and 21C.

A failure in the information compressing part 18 may arise only at a specific rotational speed or a specific rotational position. On the other hand, behavior verification of the information compressing part 18 may become difficult in the uncompressed mode since uncompressed data is output from the DAS 13 and compression processing is not performed in the information compressing part 18. Therefore, it is desirable to make it possible to verify behavior of the information compressing part 18 using compressed data acquired by rotating the rotational part 9 one time.

Accordingly, if a reference pattern mentioned above is generated for one row of X-ray detection elements, behavior verification of the information compressing part 18 using compressed data can be effectively performed by compressing and transmitting the reference pattern in a desired rotational speed and rotational angle. Furthermore, if mutually different kinds of plural reference patterns generated by plural creation methods are prepared, a behavior check of the information compressing part 18 can be performed much more effectively.

Note that, an operational verification of the information compressing part 18 using a reference pattern may be performed not only when an abnormality occurs to data but a time of daily power activation of the X-ray CT apparatus 1 or the like periodically. Also in such a case, if a reference pattern for about one row of X-ray detection elements can be stored in the DAS 13, compressed data can be transmitted in each rotational angle. Therefore, even if it is difficult to prepare a mass storage in the DAS 13, behavior verification of the information compressing part 18 using the reference pattern can be performed.

The transmitter 14 has a function to transmit transmission data, output from the DAS 13, from the rotational part 9 to the irrotational part 10 through the data transmission line 16A. Meanwhile, the receiver 15 has a function to receive the transmission data transmitted from the transmitter 14 and transmit the received transmission data to the data processing unit 5 through the data transmission line 16B.

The control unit 4 is a control device which controls the rotation of the rotational part 9 of the gantry 3 and the movement of the bed 2 according to direction information input from the console 6. By these controls, a helical scan and a scan at an arbitrary bed position can be performed. Moreover, a spatial division of uncompressed data coordinating with the rotation of the rotational part 9 can be performed in the uncompressed mode. That is, data acquisitions can be performed at a specific bed position by rotating the rotational part 9 n times under the control by the control unit 4.

The data processing unit 5 can be configured by installing a data processing program of the X-ray CT apparatus 1 into a computer. However, circuits may be used for configuring the data processing unit 5. The data processing unit 5 functions as an information uncompressing part 22, a correction processing part 23, an image reconstruction part 24, and the verification data transmitting part 21C.

The information uncompressing part 22 has a function to perform information uncompressing processing of compressed data transmitted from the DAS 13 through the transmission pathway to obtain projection data as uncompressed data. The correction processing part 23 has a function to perform necessary correction processing of the uncompressed projection data. The image reconstruction part 24 has a function to reconstruct X-ray CT image data as tomographic data of an object by image reconstruction processing of the projection data after the correction processing. The function of the verification data transmitting part 21C is as mentioned above.

Moreover, X-ray CT image data generated in the data processing unit 5 can be displayed on the display unit 7, or be written and stored in the image database 8.

The console 6 is an input device for inputting directions information into a desired element, such as the control unit 4 or the data processing unit 5, of the X-ray CT apparatus 1, by an operation of a user. Specifically, the console 6 can be composed by input devices, such as a hard key, a mouse, and an electronic key. In addition, a simple panel for displaying information may be prepared in the console 6.

Each of the data transmission lines 16A and 16B is a pathway for transmitting transmission data output from the DAS 13 to the data processing unit 5 as mentioned above. For each of the data transmission lines 16A and 16B, a transmission means to which the transmission rate required for transmitting projection data compressed into 1/n from the DAS 13 has been guaranteed is used. In the example shown in FIG. 1, the wireless data transmission line 16A is formed between the transmitter 14 in the DAS 13 side and the receiver 15 of the irrotational part 10 while the wired data transmission line 16B is formed with signal wires between the receiver 15 and the data processing unit 5.

In the X-ray CT apparatus 1 having the above mentioned elements, the information compressing part 18 of the DAS 13 and the rotational part 9 including the X-ray exposure part 11 and the X-ray detector 12 function as a data acquiring unit configured to expose an X-ray to an object, acquire detection data of the X-ray having transmitted the object and compress the detection data by a reversible compression method or an irreversible compression method to generate compressed data. Moreover, the data processing unit 5 functions as a data processing unit configured to generate X-ray T image data of the object based on the compressed data transmitted from the data acquiring unit through a transmission line.

Furthermore, the data transmission control part 20 of the DAS 13 functions as a data transmitting unit configured to transmit uncompressed detection data of an X-ray, as verification data or data for generation of X-ray CT image data of an object, to the data processing unit through the transmission line according to information from an input device. Note that, it is preferable to transmit the uncompressed X-ray detection data with a transmission rate not more than that of the compressed data.

Moreover, the data storage part 19 functions as a data storage unit configured to store a part or all of detection data of an X-ray having transmitted an object as verification data and detection data of an X-ray having transmitted an object as data for generating X-ray CT image data of the object. Therefore, the data transmission control part 20 functions as a data transmitting unit configured to transmit the verification data or the data for generating X-ray CT image data, stored in the data storage unit, with a time division to the data processing unit according to information from an input device.

Furthermore, the information compressing part 18 of the DAS 13 and the rotational part 9 including the X-ray exposure part 11 and the X-ray detector 12 also function as a data acquiring unit configured to acquire detection data of an X-ray, having transmitted an object, as spatially divided pieces of divided data according to information from an input device. Therefore, the data transmission control part 20 functions as a data transmitting unit configured to transmit the pieces of the divided data sequentially as the verification data or the data for generating X-ray CT image data to the data processing unit.

On the other hand, the verification data transmitting part 21A of the DAS 13 functions as a data transmitting unit configured to compress reference data, a compression ratio by an irreversible compression method of which is known, by the irreversible compression method according to information from an input device to transmit the compressed reference data to at least one of the data processing unit and the input device through the transmission line with a transmission rate not more than a transmission rate of the compressed data.

Note that, the X-ray CT apparatus 1 may be configured by a combination of other elements as well as the configuration illustrated in FIG. 1 so long as the X-ray CT apparatus 1 has the functions mentioned above.

Next, an operation and an action of the X-ray CT apparatus 1 will be described.

When an examination of an object is performed by the X-ray CT apparatus 1, information for selecting a mode is input into the DAS 13 to select the compressed mode by operation of the console 6. Then, the rotational part 9 with the X-ray exposure part 11 and the X-ray detector 12 rotates around the object and an X-ray is exposed toward the object from the X-ray exposure part 11. Thereby, the X-ray which has transmitted the object is detected by the X-ray detector 12, and the detected X-ray is output to the DAS 13 as X-ray detection data.

Note that, since the X-ray exposure part 11 and the X-ray detector 12 rotate around the object, X-ray detection data corresponding to mutually different rotational angles of the X-ray exposure part 11 and the X-ray detector 12 are to be detected in the X-ray detector 12. Then, the two dimensional X-ray detection data corresponding to each rotational angle is output to the DAS 13 as view data sequentially.

Next, in the signal processing part 17 of the DAS 13, projection data is generated by signal processing, such as amplification, integral processing, A/D conversion processing, and logarithmic transformation processing, of the X-ray detection data. The generated projection data is preferably compressed by the data compression processing by an irreversible compression method in the information compressing part 18. Thereby, the projection data can be transmitted to the data processing unit 5 with a low transmission rate.

For example, when the rotational part 9 of the gantry 3 rotates two times in one second to detect an X-ray 2000 times per rotation using the X-ray detector 12 having 1000 channels×250 rows of the X-ray detection elements each outputting 16 bits of data, 16 Gbit of data is input into the DAS 13. Therefore, if one examination period is 50 seconds, data for 100 rotations are acquired per one examination. Consequently, the total size of the data acquired by one examination becomes 16 Gbit×50/8 bit=100 GByte. Actually, information such as rotational positions of the gantry 3, doses of exposed X-rays and positions of the bed is added to the above mentioned data as incidental information.

Therefore, supposing that information compression is not performed, a non-contact type or an optical transmission type of a data transmission line, to which a high transmission rate allowing transmission of data having the above mentioned size has been guaranteed, is needed. In addition, a mass storage which can store the data having the above mentioned size is needed for the data processing unit 5. For this reason, the cost for the data transmission and the data storage becomes very high.

On the contrary, if a data transmission line to which a low transmission rate has been guaranteed as compared with the size of the data mentioned above is used, the transmission rate becomes insufficient. For this reason, a real time transmission of the data becomes impossible. As a result, storage for storing 100 GByte of the data is needed in the DAS 13. Therefore, the cost of the storage which should be included in the DAS 13 increases. Furthermore, about 100 seconds of time, which is twice as long as an examination time, is required for a transmission of the data.

On the other hand, the compression processing of the projection data by the information compressing part 18 makes it possible to transmit the projection data in real time with a much higher transmission rate than that in the case of transmitting the uncompressed data. For this reason, the increase in the cost of the storage which should be included in the DAS 13 and a delay in a data transmission can be avoided.

The projection data compressed in the information compressing part 18 is transmitted as the compressed data to the data processing unit 5 through the transmitter 14, the wireless data transmission line 16A, the receiver 15, and the wired data transmission line 16B. Especially, when the projection data has been compressed by an irreversible compression method, the projection data can be transmitted in real time with a transmission rate not more than the guaranteed transmission rate.

The compressed data transmitted to the data processing unit 5 are sequentially subjected to the information uncompressing processing in the information uncompressing part 22. Subsequently, the correction processing part 23 performs necessary correction processing of the uncompressed projection data obtained by the information uncompressing processing. Next, the image reconstruction part 24 performs image reconstruction processing of the projection data after the correction to reconstruct X-ray CT image data. The reconstructed X-ray CT image data can be displayed on the display unit 7. Moreover, necessary X-ray CT image data is stored in the image database 8.

On the other hand, in a case of verifying the behavior of the DAS 13, the information for selecting the mode is input into the DAS 13 to select the uncompressed mode by operation of the console 6. The behavior verification of the DAS 13 can be performed at arbitrary timing, such as timing before an imaging of a patient, a timing of the daily first boot of the X-ray CT apparatus 1, or a case where an abnormality has appeared in data. For example, at timing before an imaging of a patient or a timing of the first boot of the X-ray CT apparatus 1, data output from the X-ray detector 12 with switching an X-ray off or air calibration data is acquired as data for behavior verification in order to check the behavior of the X-ray CT apparatus 1.

Moreover, if an A/D converter included in the signal processing part 17 of the DAS 13 or the X-ray detector 12 breaks down, an abnormality sometimes occurs in data from a specific row or a specific channel. Furthermore, an abnormality in data sometimes occurs only in a specific rotational speed, such as the maximum rotational speed, or a specific rotational position.

In such a case, data for about one rotation is acquired as data for behavior verification under specific conditions in order to specify the broken device. For example, data output from the X-ray detector 12 in the case of setting an X-ray off or X-ray detection data obtained using water or a predetermined phantom as an object is acquired as the data for the behavior verification.

However, if the data for the behavior verification is compressed to be transmitted from the DAS 13, it cannot be discriminated whether an abnormality possibly arising to the data for the behavior verification is due to a compression error by an irreversible information compression or due to a failure of the X-ray detector 12 or an A/D converter.

Accordingly, the uncompressed mode is selected in a case of acquiring and transmitting the data for the behavior verification. Then, the data for the behavior verification is transmitted from the DAS 13 to the data processing unit 5 as uncompressed data without compression. Note that, the uncompressed data for the behavior verification is divided to be transmitted so that an imperfect transmission of the data may not occur by insufficiency in a transmission rate in the data transmission pathway.

Specifically, the uncompressed data for the behavior verification is subjected to a time division or a spatial division so as to be transmitted with a transmission rate not more than the transmission rate guaranteed for compressed data in the data transmission pathway. Hereinafter, the description will be made with distinguishing a case of a time division of the uncompressed data for the behavior verification from a case of a spatial division of the uncompressed data.

First, a case of a time division of the uncompressed data for the behavior verification will be described.

Figure 6:
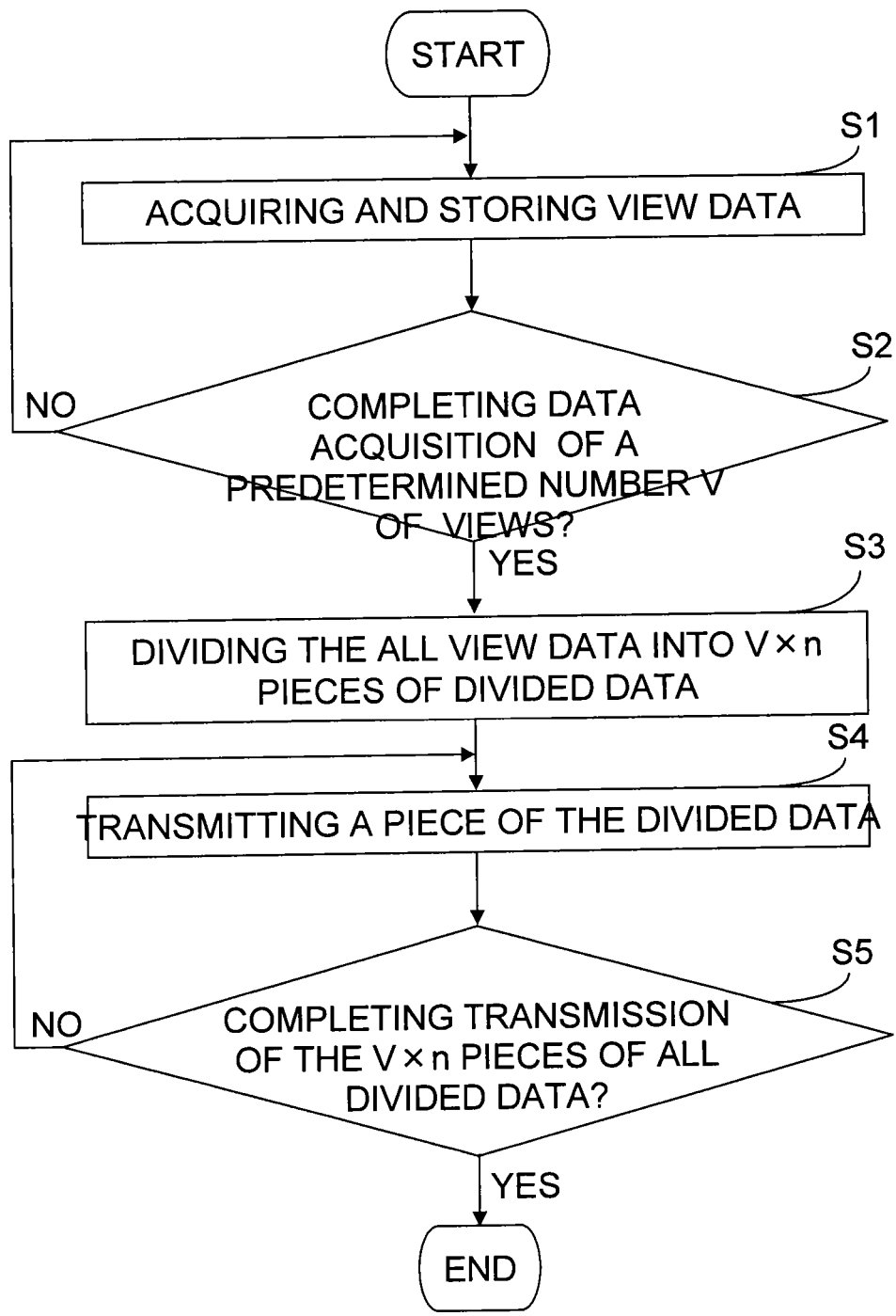
FIG. 6 is a flowchart showing a flow in the case of performing a time division of previously stored view data and a delay transmission of the time-divided view data as uncompressed verification data in the uncompressed mode of the X-ray CT apparatus shown in FIG. 1.

FIG. 6 is a flowchart showing a flow in the case of performing a time division of previously stored view data and a delay transmission of the time-divided view data as uncompressed verification data in the uncompressed mode of the X-ray CT apparatus 1 shown in FIG. 1.

First, in step S1, the rotational part 9 including the X-ray exposure part 11 and the X-ray detector 12 is rotated into a predetermined rotational angle to acquire X-ray detection data for the behavior verification as view data in a similar flow to that for the acquisition of view data in the compressed mode. The acquired view data is output from the X-ray detector 12 to the DAS 13. Subsequently, the view data is subjected to signal processing which includes the A/D conversion in the signal processing part 17. After that, the view data is stored in the data storage part 19.

Such acquisition and storage of the view data are repeated until it is discriminated that the view data corresponding to a predetermined number of views V [view] necessary for the behavior verification of the DAS 13 have been acquired in step S2. For example, if the view data for one rotation of the rotational part 9 is necessary for the behavior verification of the DAS 13, the number of rotations, rotational positions, and rotational angles, at which the view data are acquired, of the rotational part 9 are input from the console 6 to the control unit 4. Then, the rotational part 9 rotates under the control of the control unit 4. Thereby, the view data is sequentially acquired and stored in the DAS 13.

On the other hand, the number V [view] of the view data is notified from the control unit 4 to the data transmission control part 20 of the DAS 13. Then, the data transmission control part 20 performs the determination in step S2. If the data transmission control part 20 determinates that the number V [view] of the view data necessary for the behavior verification has been acquired and stored, the data transmission control part 20 divides each of all V [view] of the view data, stored in the data storage part 19, into n pieces in step S3.

As a result, V×n pieces of divided data are generated in the DAS 13. For example, one piece of the view data can be divided into n pieces of the divided data as shown in FIG. 5. Therefore, each size of the generated pieces of the divided data becomes to 1/n of the size of one piece of the view data. Note that, a division method can be predetermined by inputting directions information from the console 6 into the data transmission control part 20 through the control unit 4.

Next, in step S4, the data transmission control part 20 transmits a piece of the divided data preset as initial data to the data processing unit 5 without compression with a transmission rate not more than the guaranteed transmission rate through the transmitter 14, the data transmission line 16A, the receiver 15, and the data transmission line 16B.

Then, the transmission of the piece of the divided data is repeated until the data transmission control part 20 determinates that V×n pieces of the divided data have been transmitted in step S5. As a result, the V×n pieces of the divided data are sequentially transmitted to the data processing unit 5. That is, when the data transmission control part 20 determinates YES in the determination of step S5, the transmission of all the V [view] of the view data to the data processing unit 5 is completed.

Next, a case of performing a spatial division of the uncompressed data for the behavior verification will be described.

Figure 7:
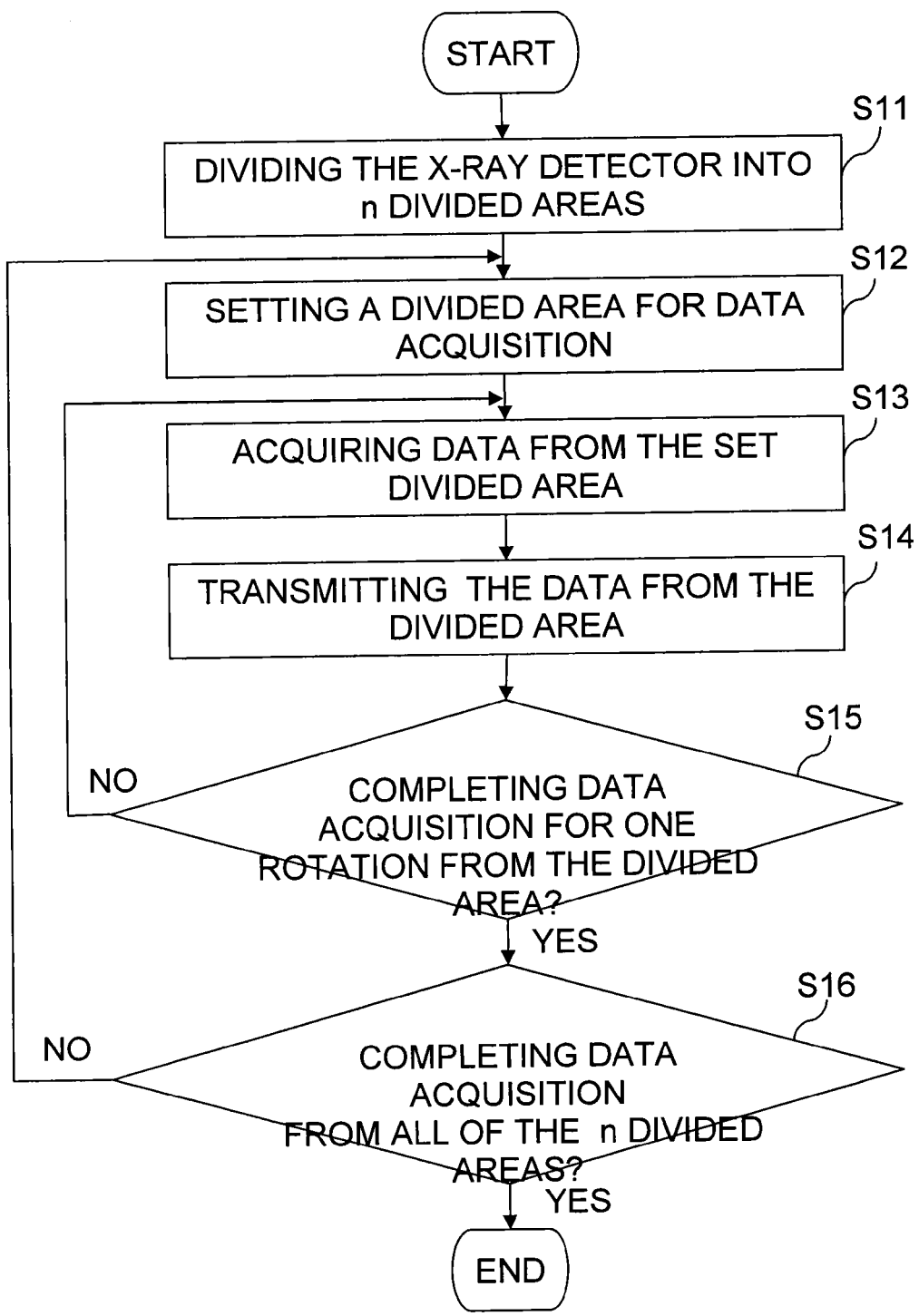
FIG. 7 is a flowchart showing a flow in the case of sequentially transmitting pieces of divided data of view data acquired with a spatial division as uncompressed verification data in the uncompressed mode of the X-ray CT apparatus shown in FIG. 1.

FIG. 7 is a flowchart showing a flow in the case of sequentially transmitting pieces of divided data of view data acquired with a spatial division as uncompressed verification data in the uncompressed mode of the X-ray CT apparatus 1 shown in FIG. 1.

Firstly, in step S11, the two dimensional region corresponding to the X-ray detection elements of the X-ray detector 12 is divided into n divided areas by the data transmission control part 20. As a concrete example, the division method as shown in FIG. 5 may be adopted. The division method can be determined by inputting directions information from the console 6 into the data transmission control part 20 through the control unit 4.

Next, in step S12, the divided area to be the first acquisition target of data is set up. The setting method of the divided area also can be determined by inputting directions information from the console 6 into the data transmission control part 20 through the control unit 4.

Next, in step S13, data is acquired from the set divided area by the drive of the rotational part 9 including the X-ray exposure part 11 and the X-ray detector 12 under the control by the control unit 4. The acquired data is output from the X-ray detector 12 to the DAS 13. Furthermore, signal processing which includes an A/D conversion is performed in the signal processing part 17.

Next, in step S14, the data transmission control part 20 transmits the data after the signal processing from the DAS 13 to the data processing unit 5 through the transmitter 14, the data transmission line 16A, the receiver 15, and the data transmission line 16B without compression with a transmission rate not more than the guaranteed transmission rate. Therefore, the data acquired from the divided area are to be transmitted to the data processing unit 5 in real time.

Then, the data acquisitions from the divided area set in step S12 and the transmissions of the acquired data to the data processing unit 5 are performed at mutually different rotational angles of the rotational part 9 until the data transmission control part 20 determinates that the data acquisitions and the transmissions of the acquired data have been completed for one rotation of the rotational part 9, in step S15.

Consequently, when the data transmission control part 20 determinates YES in step S15, the data, from the divided area set up in step S12, corresponding to one rotation of the rotational part 9, are to be transmitted to the data processing unit 5.

Furthermore, the acquisition of the data for one rotation of the rotational part 9 and the transmission of the acquired data to the data processing unit 5 are repeated with changing the divided area to be the acquisition target of data until the data transmission control part 20 determinates that the data acquisitions from all the n divided areas have been completed in step S16.

Consequently, when the data transmission control part 20 determinates YES in step S16, the data, from all the n divided areas, corresponding to one rotation of the rotational part 9, i.e., the view number V [view] of the view data corresponding to one rotation of the rotational part 9, are to be transmitted to the data processing unit 5.

Note that, the destination of the uncompressed view data, which have been subjected to the time division or the spatial division mentioned above, for the behavior verification from the DAS 13 may be the console 6 in addition to the data processing unit 5 or instead of the data processing unit 5.

When the transmission of the view data for the behavior verification is completed, a user can perform the behavior verification of the DAS 13 and the X-ray detector 12 by referring to the transmitted view data for the behavior verification. That is, if an abnormality has occurred in the view data for the behavior verification transmitted as the uncompressed data, the A/D converter and the X-ray detector 12 have a doubt of failure.

Accordingly, the view data for the behavior verification is compressed irreversibly to be transmitted from the DAS 13 to one or both of the data processing unit 5 and the console 6 subsequently. Then, the compression ratio of the transmitted view data and/or the distortion amount of the transmitted view data due to the compression is measured. Thereby, the behaviors of the DAS 13 and the X-ray detector 12 can be checked. The calculation functions of a compression ratio and a distortion amount due to a compression for that purpose have been usually provided with the DAS 13. Specifically, a failure such as an aging failure or another failure in the X-ray tube as well as a failure in the X-ray detector 12 and the DAS 13 can be detected or predicted by threshold processing of the compression ratio and/or the distortion amount due to the compression of the view data for the behavior verification.

On the other hand, if an abnormality has not occurred in the view data for the behavior verification transmitted as the uncompressed data, the A/D converter and the X-ray detector 12 have no doubt of failure. In this case, reference data of which compression ratio is known can be compressed irreversibly to be transmitted mutually from the respective verification data transmitting parts 21A, 21B, and 21C in the console 6, the data processing unit 5, and the DAS 13, as needed. Then, it can be verified whether the information compressing part 18 of the DAS 13 has a failure or not by a comparative determination of whether the transmitted reference pattern agrees with the received reference pattern or whether the compression ratio of the transmitted reference pattern agrees with that of the received reference pattern, in one of the console 6, the data processing unit 5 and the DAS 13.

Furthermore, when it is desired to generate X-ray CT image data promptly, like a case where an abnormality has appeared in data during an imaging, uncompressed data for generation of the X-ray CT image data can be transmitted from the DAS 13 to the data processing unit 5 in a similar flow to that in a case where uncompressed data for behavior verification is transmitted. The uncompressed data for generation of the X-ray CT image data can be also transmitted to the data processing unit 5 with a transmission rate not more than the transmission rate of the compressed data by a time division or a spatial division. Then, in the data processing unit 5, the X-ray CT image data can be generated by the image reconstruction processing based on the uncompressed data.

That is, the X-ray CT apparatus 1 described above is an apparatus configured to compress view data to transmit the view data from the DAS 13 to the data processing unit 5 for generating X-ray CT image data in a case of an examination of an object, and to allow transmitting the view data from the DAS 13 to the data processing unit 5 without compression for a case of behavior verification of the DAS 13 or the like, or a case where a failure has occurred in data. In addition, the X-ray CT apparatus 1 described above is an apparatus configured to allow transmitting the uncompressed view data with a transmission rate not more than the guaranteed one by a time division or a spatial division of the view data so that the transmission rate may not become insufficient in transmitting the uncompressed view data.

Further, the X-ray CT apparatus 1 described above is an apparatus configured to allow transmitting reference data, of which compression ratio is known, mutually between the console 6, the data processing unit 5, and the DAS 13 in order to verify whether the information compressing part 18 in the DAS 13 has a failure.

Therefore, according to the X-ray CT apparatus 1, whether an abnormality possibly occurring in data is caused by an information compression or the other factor can be verified promptly while the increase in the cost for the data transmission is suppressed by the information compression. That is, even if data is compressed irreversibly in the DAS 13 to be transmitted, behavior verification of the X-ray detector 12 and the DAS 13 can be performed.

Moreover, when a failure has occurred in data due to information compression processing, a transmission of uncompressed data and image reconstruction processing of X-ray CT image data using the uncompressed data can be performed promptly. Consequently, when a failure has occurred with a doubt that information compression is a factor, an examination can be restarted promptly.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray CT apparatus comprising:
   a data acquiring unit configured to expose an X-ray to an object, acquire detection data of the X-ray having transmitted the object and compress the detection data to generate compressed data;
   a data processing unit configured to generate X-ray CT image data of the object based on the compressed data transmitted from said data acquiring unit through a transmission line; and
   a data transmitting unit configured to transmit uncompressed verification data or uncompressed detection data corresponding to the detection data acquired by the data acquiring unit to said data processing unit through the transmission line when direction information has been input from an input device.

2. An X-ray CT apparatus of claim 1,
   wherein said data transmitting unit is configured to transmit the uncompressed detection data of the X-ray to said data processing unit with a transmission rate not more than a transmission rate of the compressed detection data.

3. An X-ray CT apparatus of claim 1,
   wherein said data acquiring unit is configured to compress the detection data of the X-ray by an irreversible compression method.

4. An X-ray CT apparatus of claim 3,
   wherein said data transmitting unit is configured to compress reference verification data by the irreversible compression method, when direction information has been input from the input device and to transmit the compressed reference verification data to at least one of said data processing unit and the input device through the transmission line with a transmission rate not more than a transmission rate of the compressed detection data, wherein a correct compressed characteristic for the reference verification data compressed by the irreversible compression method is preliminarily known to the at least one of said data processing unit and the input device.

5. An X-ray CT apparatus of claim 1, further comprising:
   a data storage unit configured to store a part or all of detection data of an X-ray having transmitted the object or another object as the verification data;
   wherein said data transmitting unit is configured to transmit the verification data with a time division to said data processing unit when direction information has been input from the input device, the verification data stored in said data storage unit.

6. An X-ray CT apparatus of claim 1,
   wherein said data acquiring unit is configured to acquire detection data of an X-ray having transmitted the object or another object as spatially divided pieces of divided data when direction information has been input from the input device; and
   said data transmitting unit is configured to transmit the pieces of the divided data as the verification data sequentially to said data processing unit when direction information has been input from the input device.

7. An X-ray CT apparatus of claim 1,
   wherein said data transmitting unit is configured to transmit the uncompressed detection data of the X-ray as data for generating X-ray CT image data of the object to said data processing unit.

8. An X-ray CT apparatus of claim 7, further comprising:
a data storage unit configured to store the detection data of the X-ray having transmitted the object,
wherein said data transmitting unit is configured to transmit the detection data of the X-ray with a time division to said data processing unit when direction information has been input from the input device, the detection data stored in said data storage unit.

9. An X-ray CT apparatus of claim 7,
wherein said data acquiring unit is configured to acquire the detection data of the X-ray having transmitted the object as spatially divided pieces of divided data when direction information has been input from the input device; and
said data transmitting unit is configured to transmit the pieces of the divided data as the data for generating the X-ray CT image data of the object sequentially to said data processing unit when direction information has been input from the input device.

10. An X-ray CT apparatus comprising:
a data acquiring unit configured to expose an X-ray to an object, acquire detection data of the X-ray having transmitted the object and compress the detection data by an irreversible compression method to generate compressed detection data;
a data processing unit configured to generate X-ray CT image data of the object based on the compressed detection data transmitted from said data acquiring unit through a transmission line; and
a data transmitting unit configured to compress reference verification data corresponding to the detection data by the irreversible compression method, when direction information has been input from an input device and to transmit the compressed reference verification data to at least one of said data processing unit and the input device through the transmission line with a transmission rate not more than a transmission rate of the compressed detection data, wherein a correct compression characteristic for the reference verification data compressed by the irreversible compression method is preliminarily known to the at least one of said data processing unit and the input device.

11. A data transmitting method of an X-ray CT apparatus comprising:
compressing detection data of an X-ray having transmitted an object by an irreversible compression method to generate compressed detection data;
transmitting the compressed detection data through a transmission line; and
transmitting uncompressed verification data, corresponding to the detection data, through the transmission line with a transmission rate not more than a transmission rate of the compressed detection data when direction information has been input from an input device.

12. A data transmitting method of an X-ray CT apparatus of claim 11, further comprising:
storing a part or all of detection data of an X-ray having transmitted the object or another object as the verification data,
wherein the stored verification data is transmitted with a time division when direction information has been input from the input device.

13. A data transmitting method of an X-ray CT apparatus of claim 11, further comprising:
acquiring detection data of an X-ray having transmitted the object or another object as spatially divided pieces of divided data when direction information has been input from the input device,
wherein the pieces of the divided data are transmitted sequentially as the verification data when direction information has been input from the input device.

* * * * *